US010815280B2

(12) United States Patent
Khanna et al.

(10) Patent No.: US 10,815,280 B2
(45) Date of Patent: *Oct. 27, 2020

(54) TETRAVALENT DENGUE VACCINE

(71) Applicant: International Centre for Genetic Engineering and Biotechnology, New Delhi (IN)

(72) Inventors: Navin Khanna, New Delhi (IN); Viswanathan Ramasamy, New Delhi (IN)

(73) Assignee: INTERNATIONAL CENTRE FOR GENETIC ENGINEERING AND BIOTECHNOLOGY, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/211,564

(22) Filed: Dec. 6, 2018

(65) Prior Publication Data

US 2019/0194261 A1 Jun. 27, 2019

Related U.S. Application Data

(63) Continuation of application No. 15/506,379, filed as application No. PCT/IB2015/056352 on Aug. 21, 2015, now Pat. No. 10,189,877.

(30) Foreign Application Priority Data

Sep. 1, 2014 (IN) .......................... 2478/DEL/2014

(51) Int. Cl.
*C12N 7/00* (2006.01)
*C07K 14/005* (2006.01)
(Continued)

(52) U.S. Cl.
CPC ............ *C07K 14/005* (2013.01); *A61K 39/12* (2013.01); *A61K 39/295* (2013.01); *C12N 7/00* (2013.01); *A61K 2039/505* (2013.01); *A61K 2039/6075* (2013.01); *A61K 2039/70* (2013.01); *C12N 2730/10122* (2013.01); *C12N 2730/10134* (2013.01); *C12N 2730/10151* (2013.01);
(Continued)

(58) Field of Classification Search
None
See application file for complete search history.

(56) References Cited

U.S. PATENT DOCUMENTS 4,766,205 A     8/1988  Ghosh-Dastidar
10,189,877 B2 * 1/2019  Khanna ................. A61K 39/12

FOREIGN PATENT DOCUMENTS

EP          0614465 B1     3/1999
IN        1259/DEL/2007    2/2009
(Continued)

OTHER PUBLICATIONS

Lam et al. Key concepts, strategies, and challenges in dengue vaccine development: an opportunity for sub-unit candidates? Expert Rev. Vaccines. 15(4), 483-495 (2016). (Year: 2016).*
(Continued)

*Primary Examiner* — Michelle S Horning
(74) *Attorney, Agent, or Firm* — McDonnell Boehnen Hulbert & Berghoff LLP

(57) ABSTRACT

The invention provides a recombinant polypeptide comprising the EDIII domain of each of Dengue virus serotype DENV-1, DENV-2, DENV-3, and DENV-4 linked to the N-terminal of HBsAg.

5 Claims, 11 Drawing Sheets

Figure 1:
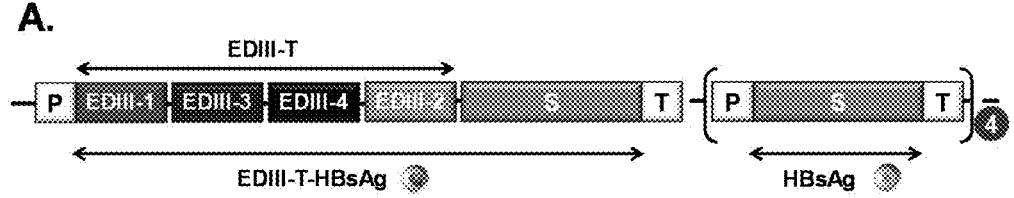
Figure 1:
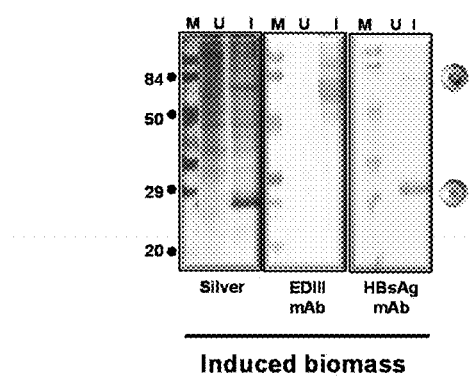
Figure 1:
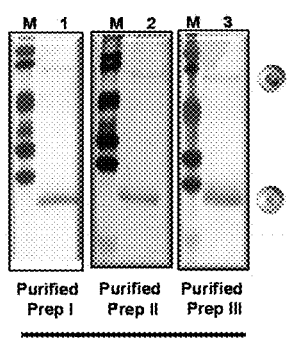

Specification includes a Sequence Listing.

(51) Int. Cl.
 *A61K 39/12* (2006.01)
 *A61K 39/295* (2006.01)
 *A61K 39/00* (2006.01)
(52) U.S. Cl.
 CPC .............. *C12N 2770/24122* (2013.01); *C12N 2770/24134* (2013.01); *C12N 2770/24151* (2013.01); *Y02A 50/386* (2018.01)

(56) References Cited

FOREIGN PATENT DOCUMENTS

| IN | 261749 | 2/2009 |
|---|---|---|
| MX | 193705 | 10/1999 |
| WO | WO 93/10152 | 5/1993 |
| WO | WO 2007/034507 A2 | 3/2007 |

OTHER PUBLICATIONS

Swaminathan and Khanna, "Dengue: Recent Advances in Biology and Current Status of Translational Research," Current Molecular Medicine, 9(2):152-173 (2009).

Guzman et al., "Domain III of the envelope protein as a dengue vaccine target," Expert Review of Vaccines, 9(2):137-147 (2010).

Simmons et al., "Evaluation of the protective efficacy of a recombinant dengue envelope B domain fusion protein against dengue 2 virus infection in mice," The American Journal of Tropical Medicine and Hygiene, 58(5):655-662 (1998).

Simmons et al., "Short report: antibody responses of mice immunized with a tetravalent dengue recombinant protein subunit vaccine," The American Journal of Tropical Medicine and Hygiene, 65(2):159-161 (2001).

Etemad et al., "An Envelope Domain III—based Chimeric Antigen Produced in Pichia pastoris Elicits Neutralizing Antibodies Against All Four Dengue Virus Serotypes," The American Journal of Tropical Medicine and Hygiene, 79(3):353-363 (2008).

Suzarte et al., "A novel tetravalent formulation combining the four aggregated domain III-capsid proteins from dengue viruses induces a functional immune response in mice and monkeys," International Immunology, 27(8):367-379 (2015).

Zuest et al., "Tetravalent dengue DIIIC protein together with alum and ODN elicits a Th1 response and neutralizing antibodies in mice," Vaccine, 33(12):1474-1482 (2015).

Izquierdo et al., "A tetravalent dengue vaccine containing a mix of domain III-P64k and domain III-capsid proteins induces a protective response in mice," Archives of Virology, 159(10):2597-2604 (2014).

Khetarpal et al., "Dengue-specific subviral nanoparticles: design, creation and characterization," Journal of Nanobiotechnology, 11(1):15, 1-8 (2013) XP021152328.

Schmitz et al., "Next generation dengue vaccines: A review of candidates in preclinical development," Vaccine, 29(42):7276-7284 (2011) XP028285287.

Mani et al., "Pichia pastoris-Expressed Dengue 2 Envelope Forms Virus-Like Particles without Pre-Membrane Protein and Induces High Titer Neutralizing Antibodies," PLOS One, 8(5):e64595, 1-9 (2013) XP055065325.

Brandler et al., "Pediatric measles vaccine expressing a dengue tetravalent antigenalicits neutralizing antibodies against all four dengue viruses", Vaccine,28:6730-6739 (2010).

Lam et al., "Key concepts, strategies, and challenges in dengue vaccine devleopment: an opportunity for sub-unit candidates?", Expert Review of Vaccines, 15(4):483-495 (2015).

Middle S Protein (Hepatitis B virus) (2010)—GenBank: ACX 69668.1 Avaliable from: https://www.ncbi.nlm.nih.gov/protein/ACX69668.1?report=genbank&log$=prottop&blast . . . , [Accessed May 26, 2018].

Structural polyprotein—Dengue virus 4—(1996)—UniProtKB—Q86654 (Q86654_9FLAV) Available from: http://www.uniprot.org/uniprot/Q86654 [Accessed May 27, 2018].

Polyprotein precursor—Dengue virus 1—(1996)—UniProtKB—Q86640 (Q88640_9FLAV) Available from: http://www.uniprot.org/uniprot/Q88640 [Accessed May 26, 2018].

Rudikoff et al., "Single Amino Acid Substitution Altering Antigen-Binding Specificity", Proc. Nat'l Acad. Sci, 79:1979-1983 (1982).

Co-pending PCT Application No. PCT/IB2015/056352, filed Aug. 21, 2015, published as WO 2016/034974 dated Mar. 10, 2016.

International Search Report and Written Opinion for International Application No. PCT/IB2015/056352, issued by EP/ISA dated Jan. 4, 2016.

International Preliminary Report on Patentability for International Application No. PCT/IB2015/056352, issued by WIPO dated Mar. 16, 2017.

Office Action for U.S. Appl. No. 15/506,379, dated Jun. 16, 2017.

Final Office Action for U.S. Appl. No. 15/506,379, dated May 31, 2018.

Office action dated Feb. 19, 2018 for European Patent Application No. 15775490.4.

Office action dated Aug. 1, 2018 for European Patent Application No. 15775490.4.

\* cited by examiner

D.

Figure 4(a)

EDIII-1 (DENV1/Nauru/West Pac/1974) SEQ ID NO:1

```
M S Y V M C T G S F K L E K E V A E T Q H G T V L V Q V K Y E
G T D A P C K I P F S S Q D E K G V T Q N G R L I T A N P I V
T D K E K P V N I E A E P P F G E S Y I V V G A G E K A L K L
S W F K K G S S I G K
```

*EDIII-1 DNA sequence* SEQ ID NO:5

```
ATG TCT TAC GTC ATG TGC ACT GGT TCT TTC AAA TTG GAG AAG GAG GTA
GCT GAA ACT CAA CAT GGC ACT GTC TTA GTT CAA GTT AAG TAC GAA GGA
ACA GAT GCC CCA TGC AAA ATC CCC TTC TCC TCC CAA GAT GAA AAG GGT
GTC ACT CAA AAT GGT AGA TTG ATA ACA GCT AAC CCA ATC GTT ACC GAC
AAG GAG AAA CCC GTG AAT ATC GAG GCC GAG CCT CCT TTC GGC GAA AGT
TAC ATA GTA GTT GGA GCC GGA GAA AAA GCA CTG AAA TTG TCT TGG TTC
AAA AAG GGT TCC TCT ATT GGA AAA
```

Figure 4(b)

EDIII-2 (DENV2/Puerto Rico/PR159-S1/1969) SEQ ID NO:2

M S Y S M C T G K F K V V K E I A E T Q H G T I V I R V Q Y E
G D G S P C K T P F E I M D L E K R H V L G R L T T V N P I V
T E K D S P V N I E A E P P F G D S Y I I I G V E P G Q L K L
D W F K K G S S I G Q

*EDIII-2 DNA sequence SEQ ID NO:6*

ATG AGT TAC TCC ATG TGC ACC GGG AAA TTC AAA GTA GTT AAA GAG
ATT GCC GAG ACT CAG CAC GGT ACA ATC GTT ATT CGA GTG CAA TAT
GAA GGT GAT GGA AGT CCA TGT AAG ACC CCA TTT GAG ATA ATG GAC
TTG GAA AAG AGG CAC GTT CTA GGG AGG TTG ACC ACT GTT AAC CCA
ATT GTG ACA GAG AAA GAT TCT CCA GTG AAT ATC GAA GCT GAA CCA
CCT TTT GGT GAT TCT TAC ATC ATT ATC GGA GTT GAA CCT GGT CAG
CTT AAG TTA GAT TGG TTC AAG AAG GGC TCC TCA ATA GGT CAG

Figure 4(c)

EDIII-3 (DENV3/Philippines/H87/1956) SEQ ID NO:3

M S Y A M C L N T F V L K K E V S E T Q H G T I L I K V E Y K
G E D A P C K I P F S T E D G Q G K A H N G R L I T A N P V V
T K K E E P V N I E A E P P F G E S N I V I G I G D K A L K I
N W Y R K G S S I G K

*EDIII-3 DNA sequence* SEQ ID NO:7

ATG AGT TAC GCC ATG TGT CTG AAT ACG TTT GTG CTT AAG AAA GAG
GTT TCT GAA ACG CAA CAC GGA ACC ATT CTT ATC AAG GTG GAA TAC
AAG GGT GAG GAC GCT CCA TGC AAG ATC CCA TTT TCT ACC GAA GAT
GGG CAG GGT AAA GCT CAT AAT GGT AGA CTG ATT ACT GCT AAT CCT
GTT GTA ACA AAG AAG GAA GAG CCA GTC AAC ATC GAG GCA GAA CCT
CCC TTT GGC GAA TCA AAC ATA GTC ATA GGG ATA GGT GAC AAG GCA
CTA AAG ATT AAC TGG TAT CGT AAG GGT TCA TCT ATT GGC AAG

Figure 4(d)

EDIII-4 (DENV4/Philippines/H241/1956) SEQ ID NO: 4

M S Y T M C S G K F S I D K E M A E T Q H G T T V V K V K Y E
G A G A P C K V P I E I R D V N K E K V V G R I I S P T P F A
E N T N S V T N I E L E R P L D S Y I V I G V G D S A L T L H
W F R K G S S I G k

*EDIII-4 DNA sequence* SEQ ID NO:8

ATG TCT TAT ACG ATG TGT TCA GGC AAG TTC TCT ATT GAC AAA GAG
ATG GCT GAA ACA CAA CAT GGT ACA ACC GTC GTT AAA GTA AAG TAT
GAA GGA GCT GGT GCA CCC TGT AAG GTG CCT ATT GAA ATT CGA GAT
GTT AAC AAA GAG AAG GTT GTC GGG AGA ATC ATT TCC CCT ACT CCA
TTT GCT GAG AAT ACT AAT TCA GTC ACT AAC ATA GAA CTA GAA CGT
CCA TTG GAC TCA TAC ATC GTA ATT GGT GTG GGA GAT TCA GCA CTT
ACT TTA CAC TGG TTT AGA AAA GGA AGT AGT ATT GGT AAA

Figure 4(e)

HbsAg (adw subtype 2) SEQ ID NO: 9

```
M E N I T S G F

Figure 4(f)

```
ATG TCT TAC GTC ATG TGC ACT GGT TCT TTC AAA TTG GAG AAG GAG GTA
 M   S   Y   V   M   C   T   G   S   F   K   L   E   K   E   V
GCT GAA ACT CAA CAT GGC ACT GTC TTA GTT CAA GTT AAG TAC GAA GGA
 A   E   T   Q   H   G   T   V   L   V   Q   V   K   Y   E   G
ACA GAT GCC CCA TGC AAA ATC CCC TTC TCC TCC CAA GAT GAA AAG GGT
 T   D   A   P   C   K   I   P   F   S   S   Q   D   E   K   G
GTC ACT CAA AAT GGT AGA TTG ATA ACA GCT AAC CCA ATC GTT ACC GAC
 V   T   Q   N   G   R   L   I   T   A   N   P   I   V   T   D
AAG GAG AAA CCC GTG AAT ATC GAG GCC GAG CCT CCT TTC GGC GAA AGT
 K   E   K   P   V   N   I   E   A   E   P   P   F   G   E   S
TAC ATA GTA GTT GGA GCC GGA GAA AAA GCA CTG AAA TTG TCT TGG TTC
 Y   I   V   V   G   A   G   E   K   A   L   K   L   S   W   F
AAA AAG GGT TCC TCT ATT GGA AAA *GGC GGT GGT GGT GGC GGA* ATG AGT
 K   K   G   S   S   I   G   K   *G   G   G   G   G   G*   M   S
TAC GCC ATG TGT CTG AAT ACG TTT GTG CTT AAG AAA GAG GTT TCT GAA
 Y   A   M   C   L   N   T   F   V   L   K   K   E   V   S   E
ACG CAA CAC GGA ACC ATT CTT ATC AAG GTG GAA TAC AAG GGT GAG GAC
 T   Q   H   G   T   I   L   I   K   V   E   Y   K   G   E   D
GCT CCA TGC AAG ATC CCA TTT TCT ACC GAA GAT GGG CAG GGT AAA GCT
 A   P   C   K   I   P   F   S   T   E   D   G   Q   G   K   A
CAT AAT GGT AGA CTG ATT ACT GCT AAT CCT GTT GTA ACA AAG AAG GAA
 H   N   G   R   L   I   T   A   N   P   V   V   T   K   K   E
GAG CCA GTC AAC ATC GAG GCA GAA CCT CCC TTT GGC GAA TCA AAC ATA
 E   P   V   N   I   E   A   E   P   P   F   G   E   S   N   I
GTC ATA GGG ATA GGT GAC AAG GCA CTA AAG ATT AAC TGG TAT CGT AAG
 V   I   G   I   G   D   K   A   L   K   I   N   W   Y   R   K
GGT TCA TCT ATT GGC AAG *GGT GGG GGA GGA GGA GGA* ATG TCT TAT ACG
 G   S   S   I   G   K   *G   G   G   G   G   G*   M   S   Y   T
ATG TGT TCA GGC AAG TTC TCT ATT GAC AAA GAG ATG GCT GAA ACA CAA
 M   C   S   G   K   F   S   I   D   K   E   M   A   E   T   Q
CAT GGT ACA ACC GTC GTT AAA GTA AAG TAT GAA GGA GCT GGT GCA CCC
 H   G   T   T   V   V   K   V   K   Y   E   G   A   G   A   P
TGT AAG GTG CCT ATT GAA ATT CGA GAT GTT AAC AAA GAG AAG GTT GTC
 C   K   V   P   I   E   I   R   D   V   N   K   E   K   V   V
GGG AGA ATC ATT TCC CCT ACT CCA TTT GCT GAG AAT ACT AAT TCA GTC
 G   R   I   I   S   P   T   P   F   A   E   N   T   N   S   V
ACT AAC ATA GAA CTA GAA CGT CCA TTG GAC TCA TAC ATC GTA ATT GGT
 T   N   I   E   L   E   R   P   L   D   S   Y   I   V   I   G
GTG GGA GAT TCA GCA CTT ACT TTA CAC TGG TTT AGA AAA GGA AGT AGT
 V   G   D   S   A   L   T   L   H   W   F   R   K   G   S   S
ATT GGT AAA *GGT GGC GGA GGT GGT GGT* ATG AGT TAC TCC ATG TGC ACC
 I   G   K   *G   G   G   G   G   G*   M   S   Y   S   M   C   T
GGG AAA TTC AAA GTA GTT AAA GAG ATT GCC GAG ACT CAG CAC GGT ACA
 G   K   F   K   V   V   K   E   I   A   E   T   Q   H   G   T
ATC GTT ATT CGA GTG CAA TAT GAA GGT GAT GGA AGT CCA TGT AAG ACC
 I   V   I   R   V   Q   Y   E   G   D   G   S   P   C   K   T
```

*Figure 4(f)-1*

```
I   V   I   R   V   Q   Y   E   G   D   G   S   P   C   K   T
CCA TTT GAG ATA ATG GAC TTG GAA AAG AGG CAC GTT CTA GGG AGG TTG
 P   F   E   I   M   D   L   E   K   R   H   V   L   G   R   L
ACC ACT GTT AAC CCA ATT GTG ACA GAG AAA GAT TCT CCA GTG AAT ATC
 T   T   V   N   P   I   V   T   E   K   D   S   P   V   N   I
GAA GCT GAA CCA CCT TTT GGT GAT TCT TAC ATC ATT ATC GGA GTT GAA
 E   A   E   P   P   F   G   D   S   Y   I   I   I   G   V   E

CCT GGT CAG CTT AAG TTA GAT TGG TTC AAG AAG GGC TCC TCA ATA GGT
 P   G   Q   L   K   L   D   W   F   K   K   G   S   S   I   G
CAG *GGA GGT GGG GGT GGA GGA GGT ACC* ATG GAA AAC ATC ACT TCC GGT
 Q  *G   G   G   G   G   G   G   T*   M   E   N   I   T   S   G
TTC TTG GGT CCT TTG TTG GTC TTG CAG GCT GGA TTC TTC TTG TTG ACT
 F   L   G   P   L   L   V   L   Q   A   G   F   F   L   L   T
AGA ATC TTG ACT ATC CCA CAG TCT TTG GAC TCT TGG TGG ACT TCC TTG
 R   I   L   T   I   P   Q   S   L   D   S   W   W   T   S   L
AAC TTC TTG GGT GGT TCC CCA GTT TGT TTG GGT CAA AAC TCC CAA TCT
 N   F   L   G   G   S   P   V   C   L   G   Q   N   S   Q   S
CCA ACT TCT AAC CAC TCC CCA ACT TCA TGT CCA CCA ATC TGT CCA GGT
 P   T   S   N   H   S   P   T   S   C   P   P   I   C   P   G
TAC AGA TGG ATG TGT TTG AGA AGA TTC ATC ATT TTC TTG TTC ATC TTG
 Y   R   W   M   C   L   R   R   F   I   I   F   L   F   I   L
TTG TTG TGT TTG ATC TTC TTG TTG GTT TTG TTG GAC TAC CAG GGT ATG
 L   L   C   L   I   F   L   L   V   L   L   D   Y   Q   G   M
TTG CCA GTT TGT CCA TTG ATT CCA GGT TCC ACT ACT ACT TCC ACT GGT
 L   P   V   C   P   L   I   P   G   S   T   T   T   S   T   G
CCA TGT AAG ACT TGT ACT ACT CCA GCT CAG GGT AAC TCT ATG TTC CCA
 P   C   K   T   C   T   T   P   A   Q   G   N   S   M   F   P
TCC TGT TGT TGT ACT AAG CCA ACT GAC GGT AAC TGT ACT TGT ATC CCA
 S   C   C   C   T   K   P   T   D   G   N   C   T   C   I   P
ATT CCT TCC TCT TGG GCT TTC GCT AAG TAC TTG TGG GAA TGG GCT TCT
 I   P   S   S   W   A   F   A   K   Y   L   W   E   W   A   S
GTT AGA TTC TCC TGG TTG TCC TTG TTG GTT CCA TTC GTT CAG TGG TTC
 V   R   F   S   W   L   S   L   L   V   P   F   V   Q   W   F
GTT GGT TTG TCT CCT ACT GTT TGG TTG TCC GCT ATC TGG ATG ATG TGG
 V   G   L   S   P   T   V   W   L   S   A   I   W   M   M   W
TAC TGG GGT CCA AGC TTG TAC TCT ATC GTT TCC CCA TTC ATC CCT TTG
 Y   W   G   P   S   L   Y   S   I   V   S   P   F   I   P   L
TTG CCA ATC TTC TTC TGT TTG TGG GTT TAC ATC TAG     SEQ ID NO:12
 L   P   I   F   F   C   L   W   V   Y   I   -      SEQ ID NO:11
```

Figure 2:
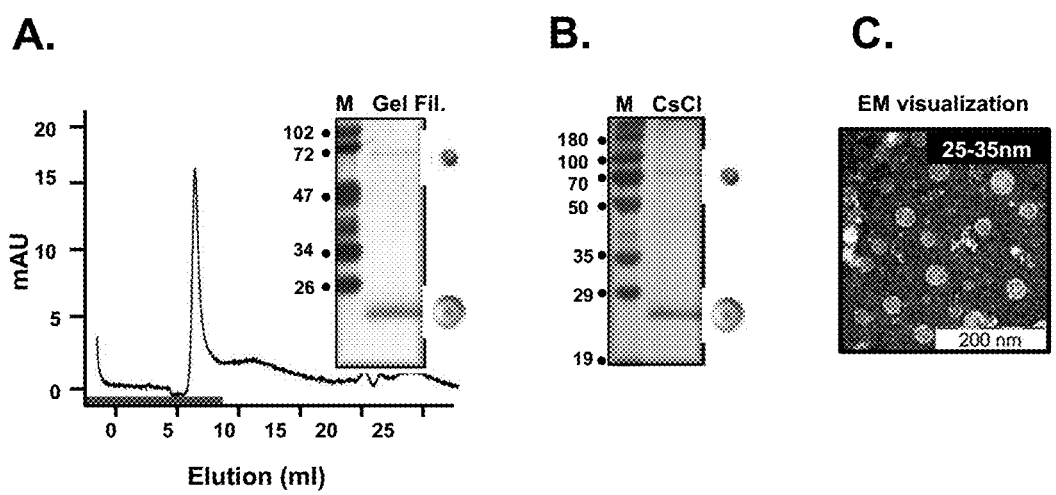

*Figure 4(f)-2*

TETRAVALENT DENGUE VACCINE

CROSS REFERENCE TO RELATED APPLICATIONS

The present application is a continuation application of Ser. No. 15/506,379 filed Feb. 24, 2017 which was filed under 35 U.S.C. § 371 as the U.S. national phase of International Application No. PCT/IB2015/056352, filed Aug. 21, 2015, which designated the U.S. and claims the benefit of priority to India Patent Application No. 2478/DEL/2014 filed 1 Sep. 2014, each of which is hereby incorporated in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Nov. 26, 2017, is named ICG006US_SEQUENCE_LISTING_ST25_2665746.txt and is 17.5 kilobytes in size.

FIELD OF THE INVENTION

The present invention relates to a recombinant dengue subunit vaccine against all the four serotypes-DENV-1, DENV-2, DENV-3, DENV-4 of Dengue. The present invention also relates to a recombinant VLP-based dengue quadrivalent vaccine candidate comprising tetravalent EDIII-T molecule and surface antigen of Hepatitis B virus (HBsAg). The present invention also relates to a process for the production of recombinant VLP (virus like particle)-based dengue quadrivalent vaccine candidate.

BACKGROUND OF THE INVENTION

Dengue disease caused by four antigenically distinct dengue viruses (DENVs) is a serious health concern in more than 150 countries of the world and especially in highly endemic countries like India. This disease has been on the rise since the last decade and has become a global public health threat because of lack of effective vaccine or antiviral therapies. Dengue disease is a global challenge for healthcare systems particularly during outbreaks, and millions of dollars are spent every year for vector control. An efficient and safe vaccine that is cost-effective could resolve the burden that dengue virus imposes on affected countries. Despite intensive efforts over the past three decades to develop a prophylactic vaccine for limiting the spread of disease, there is no licensed vaccine in the market as yet. Research groups/companies all over the world are undertaking efforts to develop an effective tetravalent vaccine against all serotypes of Dengue virus. Earlier most of the vaccines developed were based on live, attenuated, chimeric viruses and some of them are currently under clinical trials. However, due to limitations such as viral interference, the research focus has transitioned towards subunit vaccines particularly using the domain III of the envelope (E) protein of the dengue virus. Numerous patents/publications exploiting this domain have also been reported.

Though a live flavivirus based dengue vaccine has entered phase III clinical trials, problems due to viral interference have been reported. Viral interference arises presumably because of differences in replicative potential and immunogenicity of the four vaccine virus strains.

Non-replicative subunit vaccines have the potential to overcome the risk of viral interference associated with live virus vaccines [Swaminathan, Khanna, N. (2009), *Dengue: Recent advances in biology and current status of translational research, Current Mol. Med.* 9: 152-173]. Several approaches using recombinant DNA and protein based subunit vaccines are being explored. The majority of such recombinant subunit vaccines focus on the major envelope (E) protein. A number of evidences have further shown that many of the vaccine properties of the E protein are associated with domain III (EDIII).

DENV envelope domain III (EDIII) has been shown to be responsible for recognition of the host cell receptor and generation of neutralizing antibodies [Swaminathan, Khanna, N. (2009). *Dengue: Recent advances in biology and current status of translational research, Current Mol. Med.* 9: 152-173; Guzman, M. G. Hermida, L., Bernardo, L., Ramirez, R., Guillen, G. (2010). *Domain II of the envelope protein as a dengue vaccine target*]. Moreover, EDIII has been reported to have only a very low intrinsic potential for inducing cross-reactive anti-bodies [Simmons, M, Nelson, W. M, Wu, S. J., Hayes, C. G. (1998). *Evaluation of the protective efficacy of a recombinant dengue envelope B domain fusion protein against dengue 2 virus infection in mice; Am. J. Trop. Med. Hyg.* 58: 655-662; Simmons, M, Murphy, G. S., Hayes, C. G. (2001). *Short report: anti-body responses of mice immunized with a tetravalent dengue recombinant protein subunit vaccine, Am. J. Trop. Med. Hyg.* 65: 159-161]. These attributes make EDIII an excellent vaccine candidate. The efficacy of EDIII as a potential dengue vaccine antigen in the form of tetravalent protein has already been established by the inventors [Etemad, B., Batra, G., Raut, R., Dahiya, S., Khanam, S., Swaminathan, S., Khanna, N. (2008)].

Numerous patents/publications exploiting domain III of the envelope (E) protein of the dengue virus have been reported viz, Suzarte, E., Gil, L., Valdés, I., Marcos, E., Lazo, L., Izquierdo, A., . . . & Hermida, L. (2015), *International immunology, dxv011* discloses a novel tetravalent formulation combining the four aggregated domain III-capsid proteins from dengue viruses induces a functional immune response in mice and monkeys. This reference teaches a vaccine candidate against dengue virus based on two different viral regions, the domain III of the envelope protein and the capsid protein, wherein the tetravalent formulation of DIIIC proteins was used. The novel chimeric protein from dengue-2 virus (domain III-capsid (DIIIC-2)), when presented as aggregates incorporating oligodeoxynucleotides, induced antiviral and neutralizing antibodies, cellular immune response, and conferred significant protection to mice and monkeys. The remaining constructs were already obtained and properly characterized. Based on these evidences the present work was aimed at assessing the immune response in mice of the chimeric proteins DIIIC of each serotype, as monovalent and tetravalent formulations. The present inventors demonstrated the immunogenicity of each protein in terms of humoral and cell-mediated immunity, without antigen competition on the mixture forming the formulation tetra DIIIC. Accordingly, significant protection was afforded as measured by the limited viral load in the mouse encephalitis model. The assessment of the tetravalent formulation in non-human primates was also conducted. In this animal model, it was demonstrated that the formulation induced neutralizing antibodies and memory cell-mediated immune response with IFN-γ-secreting and cytotoxic capacity, regardless the route of immunization used. The tetravalent formulation of DIIIC proteins constitutes a promising vaccine candidate against dengue virus.

Zuest, R., Valdes, I., Skibinski, D., Lin, Y., Toh, Y. X, Chan, K., . . . & Fink, K. (2015), Vaccine 33(12),1474-1482 discloses the immunogenicity of a tetravalent formulation of a recombinant fusion protein consisting of E domain III and the capsid protein of dengue serotypes 1-4 (TetraDIIIC) to impart immunity against the dengue virus. E domain III is an epitope for efficient neutralizing antibodies while the capsid protein contains T cell epitopes. Besides combining B and T cell epitopes, Tetra DIIIC is highly immunogenic due to its aggregate form and a two-component adjuvant. Following previous studies assessing the monovalent DIIIC formulations, were addressed the quality and breadth of the T cell- and antibody response of Tetra DIIIC in mice. Tetra DIIIC induced a Th1-type response against all four DENV serotypes and dengue-specific antibodies were predominantly IgG1 and IgG2a and neutralizing, while the induction of neutralizing antibodies was dependent on IFN signaling. Importantly, the Th1 and IgG1/IgG2a profile of the DIIIC vaccine approach is similar to an efficient natural anti-dengue response.

Izquierdo, A., Garcia, A., Lazo, L., Gil, L., Marcos, E., Alvarez, M, & Guzmán, M. G. (2014), *Archives of Virology*, 159(10), 2597-2604 discloses a tetravalent dengue vaccine containing a mix of domain III-P64k and domain III-capsid proteins induces a protective response in mice. This reference teaches a vaccine candidate containing domain III of the dengue virus (type 1, 3 and 4) envelope protein fused to the P64k protein from *Neisseria meningitidis* and domain III of dengue virus type 2 (D2) was found to be immunogenic. Recombinant fusion proteins containing domain III of the dengue virus envelope protein fused to the P64k protein from *Neisseria meningitidis* and domain III of dengue virus type 2 (D2) fused to the capsid protein of this serotype were immunogenic and conferred protection in mice against lethal challenge in mice immunized with this tetravalent formulation were evaluated.

Live attenuated vaccines (LAVs), considered the most effective approach for dengue, have belied this expectation. Recent data from an efficacy trial of the most advanced LAV candidate showed an overall efficacy of 30%, with no efficacy for DENV-2. This necessitates serious exploration of alternate approaches to develop a dengue vaccine. VLP-based dengue quadrivalent vaccine candidate, 'DSV$^4$', is an HBsAg-based VLP displaying all the four EDIIIs corresponding to the four serotypes of DENV developed.

Initially, as disclosed in Indian Patent No. 261749, a Tetravalent Domain III protein (rTDIII), a single chimeric polypeptide comprising domain III of all four serotypes of Dengue virus, Dengue-1, 2, 3 and 4, linked with each other through penta-glycine linkers, was codon-optimised for expression in *E. coli*.

An another Indian Patent application No. 1259/DEL/2007 discloses a recombinant envelop domain-III based tetravalent protein with and without secretory signal peptide eliciting protective immune responses against each of the four serotypes of dengue virus, DEN-1, DEN-2, DEN-3 and DEN-4, the said protein encoded by a polynucloeotide sequence codon optimized for expression in eukaryotic expression system.

Ability of Hepatitis B surface antigen (HBsAg) to serve as a platform for the presentation and display of foreign epitopes is illustrated well by the success of malarial vaccine candidate RTS,S. In order to increase the immunogenicity of EDIII-T, the inventors have explored whether HBsAg could serve well for its display. Therefore, EDIII-T was cloned in fusion with HBsAg and in a background of four expression cassettes of HBsAg in *P. pastoris* vector (FIG. 1A). This design of DSV$^4$ is similar to that of RTS,S (Patent family: WO9310152 A1, MX9206574 A, EP0614465 A1, etc.), which displays malarial epitope on HBsAg VLPs.

The novelty of the present invention lies in the construct of EDIII-T with HBsAg and in a background of four expression cassettes of HBsAg in a vector. Thus, this design of EDIII-T and HBsAg (termed as "DSV$^4$"), can be deemed novel. The inventiveness of the present invention lies in the fusion of the EDIII-T with the HBsAg to increase the immunogenicity of the expressed protein by serving as a platform for presentation and for the co-expressed HBsAg protein to assemble into VLPs. A single recombinant tetravalent domain (EDIII-T) is cloned in fusion with HBsAg and co-expressed with HBsAg to form DSV$^4$ Virus Like Particles (VLPs). The subunit tetravalent vaccine DSV$^4$ generates DENV serotype specific neutralizing antibodies and is effective against each of the 4 serotypes of Dengue.

The present invention has/is expected to have the following advantages over the existing proposed vaccines.

The Sanofi live attenuated vaccines currently under Phase-3 trial require three immunizations over an extended dosing schedule (0, 6 and 12) of 12 months to elicit balanced neutralizing antibody responses to all 4 serotypes, while the Glaxo Smith Kline (in Phase 1 trials) is aiming at—2 doses 28 days apart—type of dosing schedule and Takeda (completed Phase 2 trials) with two doses separated by only three months, immunization regime. Thus, with the preliminary data, the immunization schedule of the present vaccine would be shorter than the Sanofi under-trial vaccine. Further, the present vaccine comprises EDIII-T of all the 4 DENV serotypes and HBsAg as a single recombinant protein whereas all the other vaccine candidates in trial including Sanofi's live attenuated virus vaccines are a mix of four candidates corresponding to the four serotypes.

Further, the fusion of the recombinant EDIII-T with the HBsAg would result not only in the formation of VLPs and co-expression of the recombinant immunogenic protein and the Hepatitis B surface antigen but could provide protection/immunization against Hepatitis B along with dengue. This could lead to the development of a dual vaccine, providing simultaneous immunization against all the serotypes of Dengue as well as Hepatitis B.

OBJECTS OF THE INVENTION

An important object of the present invention is to provide a dengue subunit vaccine against all the four serotypes-DENV-1, DENV-2, DENV-3, and DENV-4.

Another object of the present invention is to provide a recombinant VLP-based dengue quadrivalent vaccine candidate, DSV4.

Yet another object of the present invention is to provide a recombinant VLP based dengue quadrivalent vaccine candidate, DSV4 which generates DENV serotype specific neutralizing antibodies against each of the 4 serotypes of Dengue, DENV-1, DENV-2, DENV-3 and DENV-4.

Still another object of the present invention is to provide a process for the production of recombinant VLP-based dengue quadrivalent vaccine candidate.

A further object of the invention is to provide an efficient and safe vaccination approach against all the four serotypes of the Dengue virus.

SUMMARY OF THE INVENTION

In a first aspect the invention provides a recombinant polypeptide comprising the EDIII domain of each of Dengue virus serotype DENV-1, DENV-2, DENV-3, and DENV-4 linked to the N-terminal of HBsAg.

In a further aspect the invention provides nucleic acid sequence encoding a recombinant protein comprising the EDIII domain of Dengue virus serotype DENV-1, DENV-2, DENV-3, and DENV-4 linked to the N-terminal of HBsAg.

In a further aspect the invention provides a host cell transformed or transfected with a nucleic acid of the invention, wherein the host cell expresses HBsAg.

In a further aspect the invention provides a bio-nanoparticle comprising the recombinant polypeptide of the invention.

In a further aspect the invention provides a method of producing a bio-nanoparticle comprising the recombinant polypeptide of the invention, comprising culturing the host cell of the invention under appropriate conditions and recovering the expressed recombinant protein or bio-nanoparticle.

In a further aspect the invention provides a vaccine comprising the recombinant polypeptide of the invention.

In a further aspect, the invention provides a vaccine comprising the bio-nanoparticle of the invention.

In a further aspect the invention provides a method of treating or preventing Dengue virus, comprising administering to a subject the recombinant polypeptide of the invention, the bio-nanoparticle of the invention or the vaccine of the invention.

In a further aspect the invention provides the recombinant polypeptide of the invention, the bio-nanoparticle of the invention or the vaccine of the invention for use in treating or preventing Dengue virus.

BRIEF DESCRIPTION OF THE ACCOMPANYING DRAWINGS

FIG. 1: (A) Design of $DSV^4$: EDIII-T consisting of four EDIIIs corresponding to the four DENVs linked through hexaglycyl linker was genetically fused with HBsAg (S) to encode for EDIII-T-HBsAg, which was cloned in vector carrying four expression cassettes of HBsAg. The recombinant plasmid was linearized with Bgl II and electroporated into *P. pastoris* cells to obtain a clone co-expressing EDIII-T-HBsAg and HBsAg.

(B) Methanol induction: Uninduced (U) and induced (I) biomass of selected clone was prepared by methanol induction and analysed for expression by silver staining and western blotting. Silver stained gel shows expression of both EDIII-T-HBsAg (~72 kDa) and HBsAg (~25 kDa) in induced sample. Western blot with EDIII specific mAb detects EDIII-T-HBsAg, and with HBsAg specific mAb detects both EDIII-T-HBsAg and HBsAg.

(C) Purification of $DSV^4$: Three preps of purified $DSV^4$ from induced biomass.

FIG. 2: (A) Gel filtration chromatography of $DSV^4$: $DSV^4$ eluted in void volume when subjected to gel filtration chromatography. Analysis of protein in void volume by silver staining indicates presence of both EDIII-T-HBsAg and HBsAg.

(B) CsCl ultracentrifugation: Co-migration of EDIII-T-HBsAg and HBsAg on ultracentrifugation on CsCl column.

(C) Electron microscopic view of $DSV^4$ VLPs: 25-35 nm sized $DSV^4$ VLPs as observed on negative staining under an electron microscope.

Figure 3:
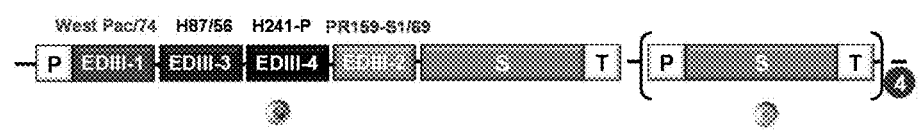
Figure 3:
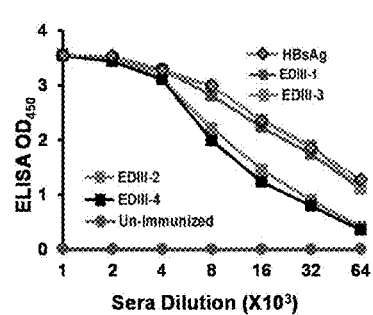
Figure 3:
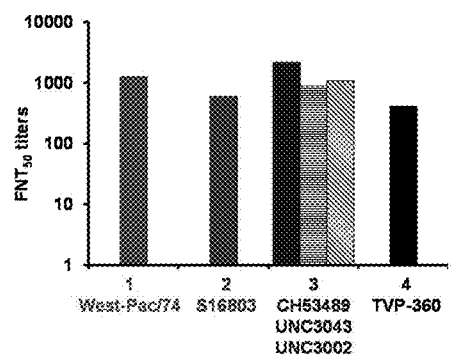
Figure 3:
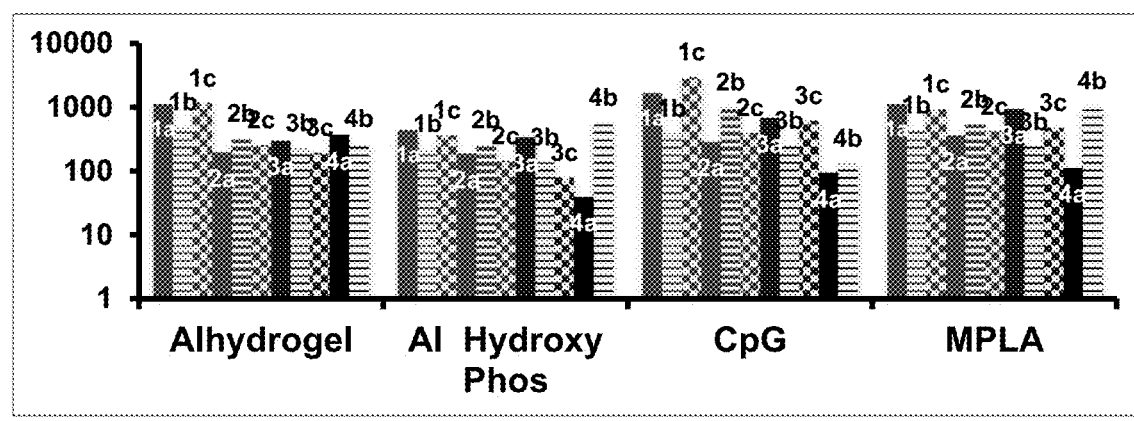

FIG. 3: (A) Source of EDIII sequence: Genotype of each DENV serotype from which corresponding EDIII aa sequence was derived.

(B) ELISA reactivity of $DSV^4$ antiserum: Reactivity of pooled $DSV^4$ antiserum against HBsAg, EDIII-1, EDIII-2, EDIII-3 and EDIII-4. Purple curve represents reactivity of un-immunized serum against $DSV^4$.

(C) $DSV^4$ generates balanced neutralizing titres: FACS-based neutralization titres of $DSV^4$ antiserum against specified genotype(s) of each serotype.

(D) Genotype neutralization breadth with pooled sera

FIG. 4: (a) the amino acid sequence of the envelope domain III of DENV-1 (SEQ ID NO:1) and the encoding nucleic acid (SEQ ID NO:5);

(b) the amino acid sequence of the envelope domain III of DENV-2 (SEQ ID NO:2) and the encoding nucleic acid (SEQ ID NO:6);

(c) the amino acid sequence of the envelope domain III of DENV-3 (SEQ ID NO:3) and the encoding nucleic acid (SEQ ID NO:7);

(d) the amino acid sequence of the envelope domain III of DENV-4 (SEQ ID NO:4) and the encoding nucleic acid (SEQ ID NO:8);

(e) the amino acid sequence of the N-terminal of HBsAg (SEQ ID NO:9) and the encoding nucleic acid (SEQ ID NO:10);

(f) the amino acid sequence of a recombinant polypeptide of the invention comprising EDIII's from DENV-1, 2, 3 and 4 linked to the N-terminal of HBsAg (SEQ ID NO:11) and the encoding nucleic acid (SEQ ID NO:12), wherein the italicized nucleic acid and amino acid sequences are hexaglycine linkers and the underlined nucleic acid and amino acid sequences are resulting from translation of KpnI restriction site. The EDIII's are sequentially order from N-terminus to C-terminus DNV-1, DNV-3, DNV-4 and DNV-2.

DETAILED DESCRIPTION OF THE INVENTION

The present invention provides a dengue subunit vaccine against all the four serotypes-DENV-1, DENV-2, DENV-3, and DENV-4 serotypes of Dengue virus. The subunit vaccine comprises a recombinant protein comprising tetravalent EDIII-T and HBsAg. The present invention also relates to a subunit vaccine comprising VLP-based quadrivalent vaccine candidate for the prevention of dengue disease against all the four serotypes of DENV.

In one aspect the invention provides a nucleic acid sequence encoding a recombinant protein comprising the EDIII domain of Dengue virus serotype DENV-1, DENV-2, DENV-3, and DENV-4 linked in frame to the N-terminal of HBsAg. The nucleotide sequences encoding each of the EDIII domains of Dengue virus serotype DENV-1, DENV-2, DENV-3, and DENV-4 can be linked with the N-terminus of HBsAg in any sequential order.

Preferably, the nucleic acid sequence encodes EDIII domains of each of Dengue virus serotype DENV-1, DENV-2, DENV-3, and DENV-4, which have the amino acid sequences of SEQ ID NO's: 1, 2, 3 and 4 respectively. Preferably, the nucleic acid sequence encoding each of the EDIII domains of Dengue virus serotype DENV-1, DENV-2, DENV-3, and DENV-4 is SEQ ID NO's: 5, 6, 7 and 8 respectively.

Preferably, the nucleic acid sequence encodes a HBsAg having the amino acid sequence of SEQ ID NO:9. Preferably, the nucleic acid sequence encoding HBsAg is SEQ ID NO:10.

In one embodiment the nucleic acid sequence comprises each of the nucleotide sequences SEQ ID NO's: 5, 6, 7 and 8 linked in frame with the N-terminus of SEQ ID NO: 10.

The nucleotide sequences SEQ ID NO's: 5, 6, 7 and 8 can be linked with the N-terminus of SEQ ID NO: 10 in any sequential order.

Preferably, the nucleic acid sequence encodes a linker that links each of the EDIII domains of Dengue virus serotype DENV-1, DENV-2, DENV-3, and DENV-4. Preferably, the nucleic acid encodes a flexible linker, most preferably a hexa-glycine linker. Preferably, the nucleic acid sequence encodes a linker that links the EDIII domains of Dengue virus serotype DENV-1, DENV-2, DENV-3, and DENV-4 to the N-terminal of HBsAg. Preferably, the nucleic acid encodes a flexible linker, most preferably a hexa-glycine linker.

Preferably, the nucleic acid sequence encodes a recombinant polypeptide having the amino acid sequence of SEQ ID NO: 11. Preferably, the nucleic acid sequence encoding the recombinant polypeptide is the nucleic acid sequence of SEQ ID NO:12.

In one embodiment the nucleic acid sequence is codon optimized for expression in yeast, preferably for expression in *P. pastoris*. In one embodiment the nucleic acid is an expression vector.

In one aspect the invention relates to a host cell transformed or transfected with a nucleic acid of the invention, wherein the host cell expresses HBsAg. In one embodiment the host cell is transformed or transfected with a nucleic acid sequence that encodes HBsAg. Preferably, the host cell is transformed or transfected with 1, 2, 3, 4 or more nucleic acid sequences expressing HBsAg. In one embodiment the host cell is a yeast. Most preferably, the host cell is *P. pastoris*.

In one aspect the invention provides a recombinant polypeptide comprising the EDIII domain of each of Dengue virus serotype DENV-1, DENV-2, DENV-3, and DENV-4 linked to the N-terminal of HBsAg. The amino acid sequences encoding each of the EDIII domains of Dengue virus serotype DENV-1, DENV-2, DENV-3, and DENV-4 can be linked with the N-terminus of HBsAg in any sequential order. Preferably, EDIII domains of Dengue virus serotype DENV-1, DENV-2, DENV-3, and DENV-4 are fused sequentially, N-terminal to C-terminal, in the sequence DENV-1, DENV-3, DENV-4 and DENV-2

Preferably, the amino acid sequence of the EDIII domains of each of Dengue virus serotype DENV-1, DENV-2, DENV-3, and DENV-4 is SEQ ID NO's: 1, 2, 3 and 4 respectively. Preferably, the N-terminal of HBsAg has the polypeptide sequence of SEQ ID NO:9. Preferably, the recombinant polypeptide comprises each of the amino acid sequences SEQ ID NO's: 1, 2, 3 and 4 linked to the N-terminus of SEQ ID NO:9. The amino acid sequences SEQ ID NO's: 1, 2, 3 and 4 can be linked with the N-terminus of SEQ ID NO: 9 in any sequential order. Preferably, the recombinant polypeptide comprises the amino acid sequences SEQ ID NO's:1, 2, 3, and 4 sequentially, N-terminal to C-terminal, in the sequence SEQ ID NO: 1, SEQ ID NO: 3, SEQ ID NO: 4 and SEQ ID NO:2.

Preferably, the EDIII domains of each of Dengue virus serotype DENV-1, DENV-2, DENV-3, and DENV-4 are linked by a linker, preferably a flexible linker, most preferably a hexa-glycine linker. Preferably, the EDIII domains are linked to the N-terminal of HBsAg by a linker, preferably a flexible linker, most preferably a hexa-glycine linker.

In one aspect the recombinant polypeptide has the amino acid sequence of SEQ ID NO: 11.

The transformed or transfected host cells of the invention synthesises both HBsAg and the recombinant polypeptide of the invention. The inventors have shown that these two polypeptides spontaneously co-assemble into bio-nanoparticle. In one aspect the invention includes bio-nanoparticle comprising HBsAg and the recombinant polypeptide of the invention of the invention.

In one aspect the invention provides a method of preparing a recombinant protein or bio-nanoparticle comprising culturing the host cell of the invention under appropriate conditions and recovering the expressed recombinant protein or bio-nanoparticle.

In one aspect, the invention relates to a vaccine comprising the recombinant polypeptide or the bio-nanoparticles of the invention. Preferably, the vaccine comprises the recombinant polypeptide or the bio-nanoparticle of the invention in a pharmaceutically acceptable carrier or suitable diluent.

In one aspect, the invention provides a method of treating or preventing Dengue virus, comprising administering to a subject a recombinant protein, a bio-nanoparticle or a vaccine of the invention. In one embodiment the Dengue virus is serotype DENV-1, DENV-2, DENV-3, or DENV-4.

The tetravalent EDIII-based molecule, EDIII-T, was developed, which was designed to contain all the four EDIIIs linked together through flexible glycyl linkers as depicted in FIG. 1A. EDIII-T was expressed in *Pichia pastoris*, purified and was found to be immunogenic in mice. The construction of the EDIII-T molecule is provided in the Indian Patent No. 261749.

The ability of surface antigen of Hepatitis B virus (HBsAg) to serve as a platform for the presentation and display of foreign epitopes is illustrated well by the success of malarial vaccine candidate RTS,S in the Patent Application No. WO 93/10152.

The present invention explores the possibilities whether HBsAg could serve to increase the immunogenicity of EDIII-T. Therefore, EDIII-T was cloned in fusion with HBsAg and in a background of four expression cassettes of HBsAg in *P. pastoris* vector as depicted in FIG. 1A. This design of EDIII-T and HBsAg is termed as "DSV$^4$" and is similar to that of RTS,S in the Patent application no. WO9310152 which displays malarial epitope on HBsAg VLPs.

The recombinant plasmid was electroporated in *P. pastoris* and the colonies were screened for the co-expression of EDIII-T-HBsAg and HBsAg proteins by methanol induction of clones. One of the positive clones co-expressing the two proteins as shown in FIG. 1B, was selected for further study. Induced biomass was lysed and the proteins associated with the membrane were extracted and subjected to diafiltration through 300 kDa membrane. This step was designed to allow enrichment of large sized protein considering that the two co-expressed proteins assemble into DSV$^4$ VLPs. The retentate was purified through phenyl 600M resin with high purity as depicted in FIG. 1C.

Ability of the co-expressed proteins to assemble into VLPs was evaluated through gel filtration as shown in FIG. 2A, CsCl Ultra-centrifugation as shown in FIG. 2B and electron microscopy as shown in FIG. 2C. It was observed that both the protein components of DSV$^4$ eluted together in the void volume during gel filtration as shown in FIG. 2A and co-migrated during CsCl ultra-centrifugation as shown in FIG. 2B. On visualization under electron microscope, they were observed to assemble into 25-35 nm VLPs as shown in FIG. 2C.

The conformational integrity of EDIII of all four DENVs in DSV$^4$ VLPs was evaluated through recognition of critical EDIII epitopes by well characterized mAbs in sandwich ELISA format.

Capability of these VLPs to mount a strong immune response against the four DENV serotypes was evaluated by immunization in BALB/c mice as shown in FIG. 3. Purified DSV$^4$ VLPs were immunized (20 µg/500 µg Al as alhydrogel/100 µl in PBS) in a group of six BALB/c mice intraperitoneally on days 0, 30 and 90. Terminal bleed was taken on day 100 and analysed for response against DSV$^4$ by ELISA. Sera from positive responders were pooled and characterized for the presence of antibodies against all its five components namely EDIII-1, EDIII-2, EDIII-3, EDIII-4 and HBsAg (FIG. 3B). It was observed that a strong immune response was generated against all of them. It was essential to determine whether anti-dengue response was capable of neutralizing the four DENVs. Therefore, the pooled serum was evaluated for its neutralization capacity through FACS-based assay and it was observed that DSV$^4$-antiserum was indeed capable of neutralizing all four DENVs (FIG. 3C). FIG. 3A illustrates the design of DSV$^4$ and the strain from which corresponding EDIII aa sequences were acquired. FIG. 3C illustrates the neutralization titre of DSV$^4$-antiserum against the four DENVs (of specified strain) and strains of two additional genotypes of DENV-3. It is evident that DENV-2, -3 and -4 genotypes used in neutralization assay varied from the genotypes from which EDIII sequence was acquired, and it did not adversely affect the neutralization capability of DSV$^4$ antiserum, indicating the high strength of the generated immune response. Moreover, the overall response against the various genotypes also appeared to be balanced, highlighting the candidacy of DSV$^4$ as a potential dengue vaccine as depicted in FIG. 3D. DSV4 appeared to be efficacious to comparable extent with various adjuvants evaluated (FIG. 3D)

The present invention is described with reference to the following examples, which are included merely to illustrate and demonstrate the invention. These specific examples should not be construed to limit the scope of the invention in any way.

EXAMPLE 1

Construction of Recombinant VLP-based Dengue Quadrivalent Vaccine Candidate

EDIII-T was cloned in fusion with HBsAg and in a background of four expression cassettes of HBsAg in *P. pastoris* vector as depicted in FIG. 1A. This design of EDIII-T and HBsAg is termed as "DSV$^4$". The recombinant plasmid was electroporated in *P. pastoris* and the colonies were screened for the co-expression of EDIII-T-HBsAg and HBsAg proteins by methanol induction of clones.

EXAMPLE 2

Characterization of Dengue Quadrivalent Vaccine Candidate-DSV$^4$

One of the positive clones co-expressing the two proteins as shown in FIG. 1B, was selected for further study. Induced biomass was lysed and the proteins associated with the membrane were extracted and subjected to diafiltration through 300 kDa membrane. This step was designed to allow enrichment of large sized protein considering that the two co-expressed proteins assemble into DSV$^4$ VLPs. The retentate was purified through phenyl 600M resin with high purity as depicted in FIG. 1C.

EXAMPLE 3

Identification and Characterization of VLPs

Ability of the co-expressed proteins to assemble into VLPs was evaluated through gel filtration as shown in FIG. 2A, CsCl Ultra-centrifugation as shown in FIG. 2B and electron microscopy as shown in FIG. 2C. It was observed that both the protein components of DSV$^4$ eluted together in the void volume during gel filtration as shown in FIG. 2A and co-migrated during CsCl ultra-centrifugation as shown in FIG. 2B. On visualization under electron microscope, they were observed to assemble into 25-35 nm VLPs as shown in FIG. 2C.

EXAMPLE 4

Evaluation of Conformational Integrity of All Four DENVs in DSV$^4$ VLPs by mAbs The conformational integrity of EDIII of all four DENVs in DSV$^4$ VLPs was evaluated through recognition of critical EDIII epitopes by well characterized mAbs in sandwich ELISA format. Dengue specific mAbs were coated in microtiter wells and DSV$^4$ VLPs were added. Bound VLPs were revealed through peroxidase labelled anti-HBsAg Hepnostika. Most of these mAbs were against A-strand and lateral ridge region of EDIII, which are believed to be essential in generating a strong neutralizing immune response. ELISA reactivity of DSV$^4$ by 21 dengue mAbs (EDIII and non-EDIII specific mAbs) is illustrated in Table 1 and the results indicate that EDIII epitopes of all four DENVs are intact in DSV$^4$ VLPs.

TABLE 1

List of EDIII-specific mAbs, regions recognized by them and their reactivity with 'DSV$^4$' VLPs (in terms of ELISA OD)

| Anti-EDIII mAbs | Strongly neutralizes | Region specificity | ELISA OD |
|---|---|---|---|
| E103 | DENV-1 | L.R-BC loop | 3.96 |
| 3H5 | DENV-2 | A.S and BC loop (L.R) | 0.77 |
| 70 | | A.S | 0.48 |
| 106 | | A.S | 0.51 |
| 104 | | C strand/CC' loop | 0.52 |
| 8A1 | DENV-3 | LR-N terminus of A.S, FG loop | 1.30 |
| E51 236 | | L.R | 1.84 |
| E51 202 | | L.R | 3.90 |
| E88 | DENV-4 | BC and DE loop (L.R) | 0.53 |
| E76 | DENV-4, -2 | N terminal A.S, CC' loop, B, D and G strands | 0.51 |
| E106 | DENV-1, -4 | A.S and L.R | 3.60 |
| E113 | DENV-1, -2, -4 | L.R | 1.20 |
| h-2J20 | DENV-1, -3 | | 2.50 |
| E61 | DENV-1, -2, -3, -4 | A.S and G strand | 0.71 |
| E77 | | A.S, BC loop and G strand | 0.81 |

| Non-EDIII mAbs | Ab type | Region specificity | ELISA OD |
|---|---|---|---|
| h-2K2 | Complex | prM | 0.06 |
| 4G2 | | Fusion Loop | 0.05 |
| h-1M7 | | | 0.06 |
| h-DVC23.13 | | | 0.05 |
| 3H4 | | | 0.05 |
| h-1N5 | | | 0.05 |

EXAMPLE 5

Immunization of Mice by Purified DSV⁴ VLPs

Capability of these VLPs to mount a strong immune response against the four DENV serotypes was evaluated by immunization in BALB/c mice as shown in FIG. 3. Purified DSV⁴ VLPs were immunized (20 μg/500 μg Al as alhydrogel/100 μl in PBS) in a group of six BALB/c mice intraperitoneally on days 0, 30 and 90. Terminal bleed was taken on day 100 and analysed for response against DSV⁴ by ELISA. Sera from positive responders were pooled and characterized for the presence of antibodies against all its five components namely EDIII-1, EDIII-2, EDIII-3, EDIII-4 and HBsAg as depicted in FIG. 3B and further Genotype neutralization breadth of DSV⁴ antisera generated with various adjuvants was determined as depicted in FIG. 3D

Immune Response

It was observed that a strong immune response was generated against all of the five components namely EDIII-1, EDIII-2, EDIII-3, EDIII-4 and HBsAg. It was essential to determine whether anti-dengue response was capable of neutralizing the four DENVs. Therefore, the pooled serum was evaluated for its neutralization capacity through FACS-based assay and it was observed that DSV⁴-antiserum was indeed capable of neutralizing all four DENVs as shown in FIG. 3C which illustrates the neutralization titre of DSV⁴-antiserum against the four WHO reference strains DENVs and strains of two additional genotypes of DENV-3. It is evident that DENV-2, -3 and -4 genotypes used in neutralization assay varied from the genotypes from which EDIII sequence was acquired, and it did not adversely affect the neutralization capability of DSV⁴ antiserum, indicating the high strength of the generated immune response. Moreover, the overall response against the various serotypes also appeared to be balanced, highlighting the candidacy of DSV⁴ as a potential dengue vaccine. Table 2 below illustrates FNT post depletion on EDIII-3-MBP eliciting serotype specific neutralizing Abs.

TABLE 2

FNT post depletion on EDIII-3-MBP elicits serotype specific neutralizing Abs

| Sera depleted on | | FNT$_{80}$-Vero | | |
|---|---|---|---|---|
| | DENV-1 | DENV-2 | DENV-3 | DENV-4 |
| Sera 1: MBP | 714 | 678 | 2259 | 415 |
| Depletion of DENV-3 Abs  EDIII-3-MSP | 1278 | 581 | 288 | 449 |
| Sera 2: MBP | nd | 775 | 1022 | nd |
| Depletion of DENV-2 Abs  EDIII-2-MSP | nd | 78 | 975 | nd |

The invention also includes the following specific aspects:

Aspect 1. A recombinant VLP-based dengue quadrivalent vaccine candidate comprising a tetravalent EDIII-T molecule and the surface antigen of Hepatitis B virus (HBsAg).

Aspect 2. A recombinant VLP-based dengue quadrivalent vaccine candidate designated DSV⁴.

Aspect 3. The recombinant VLP-based dengue quadrivalent vaccine candidate, DSV⁴, wherein the tetravalent EDIII molecule comprises EDIII of DENV-1, DENV-2, DENV-3, and DENV-4.

Aspect 4. The recombinant VLP based dengue quadrivalent vaccine candidate as recited in aspect 2 of the invention, wherein DSV⁴ generates DENV serotype specific neutralizing antibodies against DENV-1, DENV-2, DENV-3 and DENV-4.

Aspect 5. A process for the production of recombinant VLP-based dengue quadrivalent vaccine candidate as claimed in claim 1 comprises the steps of:

i) cloning of EDIII-T in fusion with HBsAg in a recombinant construct carrying four expression cassettes of HBsAg;

ii) electroporation of recombinant plasmid into *Pichia pastoris* cells to obtain a clone co-expressing EDIII-T-HBsAg and HBsAg;

iii) screening for the co-expression of EDIII-T-HBsAg and HBsAg proteins;

iv) analyzing the expression of EDIII-T-HBsAg and HBsAg proteins by silver staining and western blotting;

v) lysis of the induced biomass;

vi) extraction of the proteins associated with the membrane and subjected to diafiltration;

vii) purification of DSV⁴

Aspect 6. The process as recited in aspect 5, wherein the screening in step (iii) is done by methanol induction of clones.

Aspect 7. A dengue subunit vaccine comprising a recombinant VLP-based dengue quadrivalent vaccine candidate as recited in aspect 1.

Aspect 8. The dengue subunit vaccine as recited in aspect 7, wherein said vaccine is active against DENV-1, DENV-2, DENV-3, and DENV-4 serotypes of Dengue virus.

Aspect 9. The dengue subunit vaccine as recited in aspect 8 wherein said vaccine can be administered intraperitoneally or intramuscularly.

Aspect 10. A recombinant VLP-based dengue quadrivalent vaccine candidate for use as a dengue subunit vaccine candidate comprising of tetravalent EDIII-T molecule and the surface antigen of Hepatitis B virus (HBsAg).

SEQUENCE LISTING

<160> NUMBER OF SEQ ID NOS: 12

<210> SEQ ID NO 1
<211> LENGTH: 104
<212> TYPE: PRT
<213> ORGANISM: Dengue virus type 1

<400> SEQUENCE: 1

```
Met Ser Tyr Val Met Cys Thr Gly Ser Phe Lys Leu Glu Lys Glu Val
1               5                   10                  15

Ala Glu Thr Gln His Gly Thr Val Leu Val Gln Val Lys Tyr Glu Gly
                20                  25                  30

Thr Asp Ala Pro Cys Lys Ile Pro Phe Ser Ser Gln Asp Glu Lys Gly
            35                  40                  45

Val Thr Gln Asn Gly Arg Leu Ile Thr Ala Asn Pro Ile Val Thr Asp
        50                  55                  60

Lys Glu Lys Pro Val Asn Ile Glu Ala Glu Pro Phe Gly Glu Ser
65                  70                  75                  80

Tyr Ile Val Val Gly Ala Gly Glu Lys Ala Leu Lys Leu Ser Trp Phe
                85                  90                  95

Lys Lys Gly Ser Ser Ile Gly Lys
            100
```

```
<210> SEQ ID NO 2
<211> LENGTH: 104
<212> TYPE: PRT
<213> ORGANISM: Dengue virus type 2

<400> SEQUENCE: 2

Met Ser Tyr Ser Met Cys Thr Gly Lys Phe Lys Val Val Lys Glu Ile
1               5                   10                  15

Ala Glu Thr Gln His Gly Thr Ile Val Ile Arg Val Gln Tyr Glu Gly
                20                  25                  30

Asp Gly Ser Pro Cys Lys Thr Pro Phe Glu Ile Met Asp Leu Glu Lys
            35                  40                  45

Arg His Val Leu Gly Arg Leu Thr Thr Val Asn Pro Ile Val Thr Glu
        50                  55                  60

Lys Asp Ser Pro Val Asn Ile Glu Ala Glu Pro Pro Phe Gly Asp Ser
65                  70                  75                  80

Tyr Ile Ile Ile Gly Val Glu Pro Gly Gln Leu Lys Leu Asp Trp Phe
                85                  90                  95

Lys Lys Gly Ser Ser Ile Gly Gln
            100
```

```
<210> SEQ ID NO 3
<211> LENGTH: 104
<212> TYPE: PRT
<213> ORGANISM: Dengue virus type 3

<400> SEQUENCE: 3

Met Ser Tyr Ala Met Cys Leu Asn Thr Phe Val Leu Lys Lys Glu Val
1               5                   10                  15

Ser Glu Thr Gln His Gly Thr Ile Leu Ile Lys Val Glu Tyr Lys Gly
                20                  25                  30

Glu Asp Ala Pro Cys Lys Ile Pro Phe Ser Thr Glu Asp Gly Gln Gly
            35                  40                  45

Lys Ala His Asn Gly Arg Leu Ile Thr Ala Asn Pro Val Val Thr Lys
        50                  55                  60

Lys Glu Glu Pro Val Asn Ile Glu Ala Glu Pro Pro Phe Gly Glu Ser
65                  70                  75                  80

Asn Ile Val Ile Gly Ile Gly Asp Lys Ala Leu Lys Ile Asn Trp Tyr
                85                  90                  95

Arg Lys Gly Ser Ser Ile Gly Lys
            100
```

<210> SEQ ID NO 4
<211> LENGTH: 103
<212> TYPE: PRT
<213> ORGANISM: Dengue virus type 4

<400> SEQUENCE: 4

Met Ser Tyr Thr Met Cys Ser Gly Lys Phe Ser Ile Asp Lys Glu Met
1               5                   10                  15

Ala Glu Thr Gln His Gly Thr Thr Val Val Lys Val Tyr Glu Gly
            20                  25                  30

Ala Gly Ala Pro Cys Lys Val Pro Ile Glu Ile Arg Asp Val Asn Lys
        35                  40                  45

Glu Lys Val Val Gly Arg Ile Ile Ser Pro Thr Pro Phe Ala Glu Asn
    50                  55                  60

Thr Asn Ser Val Thr Asn Ile Glu Leu Glu Arg Pro Leu Asp Ser Tyr
65                  70                  75                  80

Ile Val Ile Gly Val Gly Asp Ser Ala Leu Thr Leu His Trp Phe Arg
                85                  90                  95

Lys Gly Ser Ser Ile Gly Lys
            100

<210> SEQ ID NO 5
<211> LENGTH: 312
<212> TYPE: DNA
<213> ORGANISM: Dengue virus type 1

<400> SEQUENCE: 5
atgtcttacg tcatgtgcac tggttctttc aaattggaga aggaggtagc tgaaactcaa    60
catggcactg tcttagttca agttaagtac gaaggaacag atgccccatg caaaatcccc   120
ttctcctccc aagatgaaaa gggtgtcact caaaatggta gattgataac agctaaccca   180
atcgttaccg acaaggagaa acccgtgaat atcgaggccg agcctccttt cggcgaaagt   240
tacatagtag ttggagccgg agaaaaagca ctgaaattgt cttggttcaa aaagggttcc   300
tctattggaa aa                                                       312

<210> SEQ ID NO 6
<211> LENGTH: 312
<212> TYPE: DNA
<213> ORGANISM: Dengue virus type 2

<400> SEQUENCE: 6
atgagttact ccatgtgcac cgggaaattc aaagtagtta agagagattgc cgagactcag    60 cacggtacaa tcgttattcg agtgcaatat gaaggtgatg gaagtccatg taagaccccca   120 tttgagataa tggacttgga aaagaggcac gttctaggga ggttgaccac tgttaaccca   180
attgtgacag agaaagattc tccagtgaat atcgaagctg aaccaccttt tggtgattct   240
tacatcatta tcggagttga acctggtcag cttaagttag attggttcaa gaagggctcc   300
tcaataggtc ag                                                       312

<210> SEQ ID NO 7
<211> LENGTH: 312
<212> TYPE: DNA
<213> ORGANISM: Dengue virus type 3

<400> SEQUENCE: 7
atgagttacg ccatgtgtct gaatacgttt gtgcttaaga aagaggtttc tgaaacgcaa    60

-continued

```
cacggaacca ttcttatcaa ggtggaatac aagggtgagg acgctccatg caagatccca    120 tttctaccg aagatgggca gggtaaagct cataatggta gactgattac tgctaatcct    180
gttgtaacaa agaaggaaga gccagtcaac atcgaggcag aacctcccctt tggcgaatca   240 aacatagtca tagggatagg tgacaaggca ctaaagatta actggtatcg taagggttca   300
tctattggca ag                                                       312
```

<210> SEQ ID NO 8
<211> LENGTH: 309
<212> TYPE: DNA
<213> ORGANISM: Dengue virus type 4

<400> SEQUENCE: 8

```
atgtcttata cgatgtgttc aggcaagttc tctattgaca aagagatggc tgaaacacaa    60
catggtacaa ccgtcgttaa agtaaagtat gaaggagctg gtgcaccctg taaggtgcct   120
attgaaattc gagatgttaa caaagagaag gttgtcggga aatcatttc ccctactcca    180 tttgctgaga atactaattc agtcactaac atagaactag aacgtccatt ggactcatac   240
atcgtaattg gtgtgggaga ttcagcactt actttacact ggtttagaaa aggaagtagt   300
attggtaaa                                                           309
```

<210> SEQ ID NO 9
<211> LENGTH: 226
<212> TYPE: PRT
<213> ORGANISM: Hepatitis B virus

<400> SEQUENCE: 9

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

<210> SEQ ID NO 10
<211> LENGTH: 678
<212> TYPE: DNA
<213> ORGANISM: Hepatitis B virus

<400> SEQUENCE: 10

```
atggaaaaca tcacttccgg tttcttgggt cctttgttgg tcttgcaggc tggattcttc      60
ttgttgacta gaatcttgac tatcccacag tctttggact cttggtggac ttccttgaac     120
ttcttgggtg gttccccagt ttgtttgggt caaaactccc aatctccaac ttctaaccac     180
tccccaactt catgtccacc aatctgtcca ggttacagat ggatgtgttt gagaagattc     240
atcattttct tgttcatctt gttgttgtgt ttgatcttct gttggttttt gttggactac     300
cagggtatgt tgccagtttg tccattgatt ccaggttcca ctactactc cactggtcca      360
tgtaagactt gtactactcc agctcagggt aactctatgt tcccatcctg ttgttgtact     420
aagccaactg acggtaactg tacttgtatc ccaattcctt cctcttgggc tttcgctaag     480
tacttgtggg aatgggcttc tgttagattc cctggttgt ccttgttggt tccattcgtt      540
cagtggttcg ttggtttgtc tcctactgtt tggttgtccg ctatctggat gatgtggtac     600
tggggtccaa gcttgtactc tatcgtttcc ccattcatcc ctttgttgcc aatcttcttc     660
tgtttgtggg tttacatc                                                   678
```

<210> SEQ ID NO 11
<211> LENGTH: 667
<212> TYPE: PRT
<213> ORGANISM: Artificial Sequence
<220> FEATURE:
<223> OTHER INFORMATION: Recombinant polypeptide of the invention

<400> SEQUENCE: 11

```
Met Ser Tyr Val Met Cys Thr Gly Ser Phe Lys Leu Glu Lys Glu Val
1               5                   10                  15
Ala Glu Thr Gln His Gly Thr Val Leu Val Gln Val Lys Tyr Glu Gly
            20                  25                  30
Thr Asp Ala Pro Cys Lys Ile Pro Phe Ser Ser Gln Asp Glu Lys Gly
        35                  40                  45
Val Thr Gln Asn Gly Arg Leu Ile Thr Ala Asn Pro Ile Val Thr Asp
    50                  55                  60
Lys Glu Lys Pro Val Asn Ile Glu Ala Glu Pro Phe Gly Glu Ser
65                  70                  75                  80
Tyr Ile Val Val Gly Ala Gly Glu Lys Ala Leu Lys Leu Ser Trp Phe
                85                  90                  95
Lys Lys Gly Ser Ser Ile Gly Lys Gly Gly Gly Gly Gly Met Ser
            100                 105                 110
Tyr Ala Met Cys Leu Asn Thr Phe Val Leu Lys Lys Glu Val Ser Glu
        115                 120                 125
Thr Gln His Gly Thr Ile Leu Ile Lys Val Glu Tyr Lys Gly Glu Asp
    130                 135                 140
Ala Pro Cys Lys Ile Pro Phe Ser Thr Glu Asp Gly Gln Gly Lys Ala
145                 150                 155                 160
His Asn Gly Arg Leu Ile Thr Ala Asn Pro Val Val Thr Lys Lys Glu
                165                 170                 175
```

```
Glu Pro Val Asn Ile Glu Ala Glu Pro Pro Phe Gly Glu Ser Asn Ile
            180                 185                 190

Val Ile Gly Ile Gly Asp Lys Ala Leu Lys Ile Asn Trp Tyr Arg Lys
        195                 200                 205

Gly Ser Ser Ile Gly Lys Gly Gly Gly Gly Gly Met Ser Tyr Thr
    210                 215                 220

Met Cys Ser Gly Lys Phe Ser Ile Asp Lys Glu Met Ala Glu Thr Gln
225                 230                 235                 240

His Gly Thr Thr Val Val Lys Val Lys Tyr Glu Gly Ala Gly Ala Pro
                245                 250                 255

Cys Lys Val Pro Ile Glu Ile Arg Asp Val Asn Lys Glu Lys Val Val
            260                 265                 270

Gly Arg Ile Ile Ser Pro Thr Pro Phe Ala Glu Asn Thr Asn Ser Val
        275                 280                 285

Thr Asn Ile Glu Leu Glu Arg Pro Leu Asp Ser Tyr Ile Val Ile Gly
    290                 295                 300

Val Gly Asp Ser Ala Leu Thr Leu His Trp Phe Arg Lys Gly Ser Ser
305                 310                 315                 320

Ile Gly Lys Gly Gly Gly Gly Gly Met Ser Tyr Ser Met Cys Thr
                325                 330                 335

Gly Lys Phe Lys Val Val Lys Glu Ile Ala Glu Thr Gln His Gly Thr
            340                 345                 350

Ile Val Ile Arg Val Gln Tyr Glu Gly Asp Gly Ser Pro Cys Lys Thr
        355                 360                 365

Pro Phe Glu Ile Met Asp Leu Glu Lys Arg His Val Leu Gly Arg Leu
    370                 375                 380

Thr Thr Val Asn Pro Ile Val Thr Glu Lys Asp Ser Pro Val Asn Ile
385                 390                 395                 400

Glu Ala Glu Pro Pro Phe Gly Asp Ser Tyr Ile Ile Gly Val Glu
                405                 410                 415

Pro Gly Gln Leu Lys Leu Asp Trp Phe Lys Lys Gly Ser Ser Ile Gly
            420                 425                 430

Gln Gly Gly Gly Gly Gly Gly Thr Met Glu Asn Ile Thr Ser Gly
        435                 440                 445

Phe Leu Gly Pro Leu Leu Val Leu Gln Ala Gly Phe Phe Leu Leu Thr
450                 455                 460

Arg Ile Leu Thr Ile Pro Gln Ser Leu Asp Ser Trp Trp Thr Ser Leu
465                 470                 475                 480

Asn Phe Leu Gly Gly Ser Pro Val Cys Leu Gly Gln Asn Ser Gln Ser
                485                 490                 495

Pro Thr Ser Asn His Ser Pro Thr Ser Cys Pro Pro Ile Cys Pro Gly
            500                 505                 510

Tyr Arg Trp Met Cys Leu Arg Arg Phe Ile Ile Phe Leu Phe Ile Leu
        515                 520                 525

Leu Leu Cys Leu Ile Phe Leu Leu Val Leu Leu Asp Tyr Gln Gly Met
    530                 535                 540

Leu Pro Val Cys Pro Leu Ile Pro Gly Ser Thr Thr Thr Ser Thr Gly
545                 550                 555                 560

Pro Cys Lys Thr Cys Thr Thr Pro Ala Gln Gly Asn Ser Met Phe Pro
                565                 570                 575

Ser Cys Cys Cys Thr Lys Pro Thr Asp Gly Asn Cys Thr Cys Ile Pro
            580                 585                 590

Ile Pro Ser Ser Trp Ala Phe Ala Lys Tyr Leu Trp Glu Trp Ala Ser
```

```
            595                 600                 605
Val Arg Phe Ser Trp Leu Ser Leu Leu Val Pro Phe Val Gln Trp Phe
        610                 615                 620

Val Gly Leu Ser Pro Thr Val Trp Leu Ser Ala Ile Trp Met Met Trp
625                 630                 635                 640

Tyr Trp Gly Pro Ser Leu Tyr Ser Ile Val Ser Pro Phe Ile Pro Leu
                645                 650                 655

Leu Pro Ile Phe Phe Cys Leu Trp Val Tyr Ile
            660                 665

<210> SEQ ID NO 12
<211> LENGTH: 2004
<212> TYPE: DNA
<213> ORGANISM: Artificial Sequence
<220> FEATURE:
<223> OTHER INFORMATION: Nucleic acid sequence of the recombinant
      polypeptide of the invention

<400> SEQUENCE: 12
atgtcttacg tcatgtgcac tggttctttc aaattggaga aggaggtagc tgaaactcaa      60
catggcactg tcttagttca agttaagtac gaaggaacag atgccccatg caaaatcccc     120
ttctcctccc aagatgaaaa gggtgtcact caaaatggta gattgataac agctaaccca     180
atcgttaccg acaaggagaa acccgtgaat atcgaggccg agcctccttt cggcgaaagt     240
tacatagtag ttggagccgg agaaaaagca ctgaaattgt cttggttcaa aagggttcc      300 tctattggaa aaggcggtgg tggtggcgga atgagttacg ccatgtgtct gaatacgttt     360
gtgcttaaga agaggtttc tgaaacgcaa cacggaacca ttcttatcaa ggtggaatac     420
aagggtgagg acgctccatg caagatccca ttttctaccg aagatgggca gggtaaagct     480
cataatggta gactgattac tgctaatcct gttgtaacaa agaaggaaga gccagtcaac     540
atcgaggcag aacctccctt tggcgaatca aacatagtca tagggatagg tgacaaggca     600
ctaaagatta actggtatcg taagggttca tctattggca agggtggggg aggaggagga     660
atgtcttata cgatgtgttc aggcaagttc tctattgaca agagatggc tgaaacacaa     720 catggtacaa ccgtcgttaa agtaaagtat gaaggagctg gtgcaccctg taaggtgcct     780
attgaaattc gagatgttaa caaagagaag gttgtcggga gaatcatttc ccctactcca     840
tttgctgaga atactaattc agtcactaac atagaactag aacgtccatt ggactcatac     900
atcgtaattg gtgtgggaga ttcagcactt actttacact ggtttagaaa aggaagtagt     960
attggtaaag gtggcggagg tggtggtatg agttactcca tgtgcaccgg gaaattcaaa    1020
gtagttaaag agattgccga gactcagcac ggtacaatcg ttattcgagt gcaatatgaa    1080
ggtgatggaa gtccatgtaa gaccccattt gagataatgg acttggaaaa gaggcacgtt    1140
ctagggaggt tgaccactgt taacccaatt gtgacagaga agattctcc agtgaatatc     1200 gaagctgaac accttttttgg tgattcttac atcattatcg gagttgaacc tggtcagctt    1260
aagttagatt ggttcaagaa gggctcctca ataggtcagg gaggtggggg tggaggaggt    1320
accatggaaa acatcacttc cggtttcttg ggtcctttgt tggtcttgca ggctggattc    1380
ttcttgttga ctagaatctt gactatccca cagtcttttgg actcttggtg acttccttg    1440 aacttcttgg gtggttcccc agtttgtttg ggtcaaaact cccaatctcc aacttctaac    1500
cactccccaa cttcatgtcc accaatctgt ccaggttaca gatggatgtg ttgagaagaa    1560
ttcatcattt tcttgttcat cttgttgttg tgtttgatct tcttgttggt tttgttggac    1620
```

```
taccagggta tgttgccagt ttgtccattg attccaggtt ccactactac ttccactggt    1680
ccatgtaaga cttgtactac tccagctcag ggtaactcta tgttcccatc ctgttgttgt    1740
actaagccaa ctgacggtaa ctgtacttgt atcccaattc cttcctcttg ggctttcgct    1800
aagtacttgt gggaatgggc ttctgttaga ttctcctggt tgtccttgtt ggttccattc    1860
gttcagtggt tcgttggttt gtctcctact gtttggttgt ccgctatctg gatgatgtgg    1920
tactggggtc caagcttgta ctctatcgtt tccccattca tccctttgtt gccaatcttc    1980
ttctgtttgt gggtttacat ctag                                            2004
```

The invention claimed is:

1. A tetravalent dengue vaccine comprising a virus like particle (VLP) comprising:
   a. a recombinant polypeptide comprising an ED III domain of each of Dengue virus serotypes DENV-1, DENV-2, DENV-3, and DENV-4, linked to an N-terminal of an HBsAg polypeptide, as depicted below:
   EDIII- 1---EDIII-3---EDIII-4---EDIII-2---HBsAg;
   wherein the dashed dashed line is a linker; and
   wherein the amino acid sequence of the ED III domains of each of Dengue virus serotypes DENV-1, DENV-2, DENV-3, and DENV-4 is SEQ ID NO's 1, 2, 3 and 4, respectively; and
   b. 4 units of an HBsAg polypeptide.

2. A method of eliciting neutralizing antibody titer against each of the four dengue virus serotypes DENV-1, DENV-2, DENV-3 and DENV-4 in a subject in need thereof comprising administering to the subject the tetravalent dengue vaccine of claim 1.

3. A method of treating or preventing dengue virus infection comprising administering to a subject the tetravalent dengue vaccine of claim 1.

4. A method for eliciting neutralizing antibody titer against each of the four dengue virus serotypes DENV-1, DENV-2, DENV-3 and DENV-4 in a subject, the method comprising:
   administering the tetravalent dengue virus vaccine of claim 1 to the subject.

5. A method for treating or preventing dengue virus infection in a subject, the method comprising:
   administering the tetravalent dengue virus vaccine of claim 1 to the subject.

* * * * *